(12) United States Patent
Kokkinis

(10) Patent No.: US 11,241,408 B2
(45) Date of Patent: Feb. 8, 2022

(54) OMEGA-3 COMPOSITIONS AND METHODS RELATING THERETO

(71) Applicant: Pharmako Biotechnologies PTY Limited, Cromer (AU)

(72) Inventor: George Kokkinis, Neutral Bay (AU)

(73) Assignee: Pharmako Biotechnologies PTY Limited, Frenchs Forest (AU)

( * ) Notice: Subject to any disclaimer, the term of this patent is extended or adjusted under 35 U.S.C. 154(b) by 0 days.

(21) Appl. No.: 16/324,947

(22) PCT Filed: Aug. 11, 2017

(86) PCT No.: PCT/AU2017/050850
§ 371 (c)(1),
(2) Date: Feb. 12, 2019

(87) PCT Pub. No.: WO2018/027278
PCT Pub. Date: Feb. 15, 2018

(65) Prior Publication Data
US 2019/0374494 A1    Dec. 12, 2019

(30) Foreign Application Priority Data

Aug. 12, 2016    (AU) .............................. 2016903184

(51) Int. Cl.
*A61K 31/202*    (2006.01)
*A61K 9/107*    (2006.01)
*A61K 47/10*    (2017.01)
*A61K 47/14*    (2017.01)
*A61K 47/26*    (2006.01)
*A61K 47/44*    (2017.01)

(52) U.S. Cl.
CPC ............ *A61K 31/202* (2013.01); *A61K 9/107* (2013.01); *A61K 47/10* (2013.01); *A61K 47/14* (2013.01); *A61K 47/26* (2013.01); *A61K 47/44* (2013.01)

(58) Field of Classification Search
CPC ...... A61K 31/202; A61K 9/107; A61K 47/10; A61K 47/14; A61K 47/26; A61K 47/44
See application file for complete search history.

(56) References Cited

U.S. PATENT DOCUMENTS

2012/0088829 A1    4/2012    Berl

FOREIGN PATENT DOCUMENTS

WO    2013148136 A1    10/2013
WO    2016057915 A1    4/2016

*Primary Examiner* — Savitha M Rao
*Assistant Examiner* — Gregg Polansky
(74) *Attorney, Agent, or Firm* — Lowenstein Sandler LLP

(57) ABSTRACT

The present invention provides for a water-soluble composition comprising at least one source of Omega-3 comprising at least one Omega-3 fatty acid selected from eicosapentaenoic acid (EPA), docosahexaenoic acid (DHA), docosapentaenoic acid (DPA) and alpha-linolenic acid (ALA), and micelle-promoting agents comprising one or more of carrier oils, solvents, emulsifiers and antioxidants, in order to promote an increase in bioavailability of the Omega-3 Source of at least two times.

19 Claims, 2 Drawing Sheets

OMEGA-3 COMPOSITIONS AND METHODS RELATING THERETO

PRIORITY APPLICATION

The present application is the U.S. national phase under 35 U.S.C. 371 of international patent application number PCT/AU2017/050850 filed on Aug. 11, 2017, which designated the U.S., and which draws priority from Australian Patent No. 2016903184, the entirety of which is incorporated herein by reference.

TECHNICAL FIELD

The present invention generally relates to water-dispersible compositions of bioactive lipophilic compounds, particularly relating to water dispersible compositions of fatty acids, their esters and triglycerides, to compounds useful for the preparation of such compositions, to methods of preparing such compounds and compositions, and to the use of such compositions as therapeutics, complementary medicines and cosmetics.

BACKGROUND

The cells of the small intestine are covered with a microscopically fine water film so that the cells can directly absorb substances that are soluble in this water film. The bioavailability of water soluble substances, such as sugar, salts, and certain water-soluble vitamins (for instance Vitamin C) is therefore at an optimum. However, fat soluble substances—such as fatty acids—are unable to penetrate the water film. Indeed, many important bioactive compounds are highly lipophilic and are suited to dissolution in non-polar solvents, while being substantially insoluble or only partially soluble in aqueous solvents. The lack of solubility of a bioactive compound in aqueous media is an important factor limiting its therapeutic use or use in clinical applications, making it difficult to efficiently administer the compound to a patient. When administered in the form of an oil solution or some kind of water and/or oil suspension or emulsion, lipophilic compounds typically show a poor bioavailability, meaning a low concentration and a long build-up time of the compound in the systemic circulation.

The physiological process conducted by the body in an attempt to absorb these lipophilic compounds of value is known as micelle formation. Through interaction with chemicals carried in bile, the lipophilic species can be 'enveloped' in a micelle. The chemicals act as surfactants and are molecules formed from a long lipophilic tail with a hydrophilic head. A typical micelle in aqueous solution forms an aggregate with the hydrophilic "head" regions in contact with surrounding solvent, sequestering the hydrophobic single-tail regions in the micelle centre. The micelle can then be dispersed in the bulk solvent by virtue of the hydrophilic head groups that form the outer layer of the micelle.

However, the micelle formation in the small intestine occurs at a time delay, being after the release of bile secretion (bile juice) and enzymes of the pancreas. Yet the rest of the digestive processes (transport, etc.) continue without interruption during the comparatively lengthy micelle formation process in the small intestine. This results in a significant proportion of the micelles being expelled as waste by the body because the micelles are formed too late in the digestion process and thus pass beyond the small intestine. The result of this is a very low bio-availability of fat-soluble substances, being typically approximately 15-25 percent of the consumed amount.

In order to ensure that a sufficient amount of the particular lipophilic substances are taken up by the body to actually produce a therapeutic benefit, they are typically required to be taken in amounts greater than 1 gram daily. This is partly due to their low aqueous solubility and thus low ability to be taken up by the body during digestion.

There are also certain people who, due to medical reasons, cannot form micelles, even further lowering their body's absorption of essential lipophilic species. Further, old age is also known to reduce the ability of a person's digestive tract to take up a range of important chemicals, including fatty acids or other lipophilic compounds enclosed in micelles.

Bioactive lipophilic compounds in need of increased solubility to aid in absorption by the body can belong to various therapeutic categories, such as certain vitamins, antibiotics, free radical scavengers, immunosuppressants and some fatty acids. Various approaches to achieve the solubility and improve the bio-availability of these and other lipophilic compounds are known in the prior art, including formation of water-soluble complexes. One particularly important class of bioactive lipophilic compound is the Omega-3 fatty acid group—particularly the Omega-3 fatty acids derived from fish oils, such as eicosapentaenoic acid (EPA), docosahexaenoic acid (DHA), docosapentaenoic acid (DPA) and alpha-linolenic acid (ALA). EPA, DHA, DPA and ALA are used, in conjunction with dietary changes, to assist in the lowering and continued control of triglyceride levels. EPA is also known or considered to be an effective treatment for a number of medical conditions and has been found to reduce the risk of heart attacks and strokes, slow the build-up of atherosclerotic plaque and reducing angina. However, the typical Western diet does not typically provide sufficient levels of Omega-3 fatty acids, necessitating the use of supplements to provide the required amounts.

Therefore it would be advantageous to provide optimised compositions of bioactive lipophilic compounds, particularly relating to compositions of Omega-3 fatty acids, including EPA, DHA, DPA and ALA, that provide an increased bioavailability of the Omega-3 fatty acid. This would overcome at least some of the disadvantages of previously known approaches in this field, or would provide a useful alternative.

DISCLOSURE OF INVENTION

These and other advantages are met with the present invention, which in one broad form comprises water-dispersible composition comprising at least one source of Omega-3, and micelle-promoting agents comprising one or more of carrier oils, solvents, emulsifiers and antioxidants, wherein the composition promotes at least a twofold increase in bioavailability of the Omega-3 source.

In an embodiment of the present invention, the composition promotes at least a threefold increase in bioavailability of the Omega-3 source. In a further embodiment of the present invention, the composition promotes at least a fourfold increase in bioavailability of the Omega-3 source.

In an embodiment of the present invention, the percentage composition of the Omega-3 source and at least one micelle-promoting agents is such that, dispersed in an aqueous environment, the composition forms a population of micelles with a mean population diameter of about 1 to 20 micrometres. More preferably, the mean population diameter of the micelles is less than about 15 micrometres. In a preferred embodiment, the mean population diameter of the micelles is greater than about 5 micrometres. More preferably, the mean population diameter of the micelles is greater than about 10 micrometres. In a most preferred embodiment of the present invention, the mean population diameter of the micelles is between about 12 to 13 micrometres.

In an embodiment of the present invention, the percentage population of micrometres with a diameter of less than 10 micrometres is greater than 20%. More preferably, the percentage population of micrometres with a diameter of less than 10 micrometres is greater than 30%. In a most preferred embodiment of the present invention, the percentage population of micrometres with a diameter of less than 10 micrometres is greater than 40%.

In an embodiment of the present invention, the Omega-3 Source comprises at least one Omega 3 fatty acid selected from eicosapentaenoic acid (EPA), docosahexaenoic acid (DHA), docosapentaenoic acid (DPA) and alpha-linolenic acid (ALA). Preferably, the Omega 3 fatty acid is present in one or more forms selected from fatty acids, ethyl esters, triglycerides and phospholipids.

In an embodiment of the present invention, the carrier oil is selected from one or more of medium chain triglycerides, long chain triglycerides, caprylic and/or capric triglycerides, coconut oil, corn oil, cottonseed oil, olive oil, sesame oil, soybean oil, peanut oil, castor oil and oleic acid.

In an embodiment of the present invention, the solvent is selected from one or more of citrus oil, ethanol, ethyl oleate, glycerine, glyceryl mono-oleate, limonene, polyethylene glycol 300, polyethylene glycol 400, polyethylene glycol 600 and propylene glycol.

In an embodiment of the present invention, the emulsifier is selected from one or more of hydrogenated castor oil, lecithin, macrogolglycerol hydroxystearate, oat oil polar lipids, phosphatidylcholine, poloxamers, polyoxyl 35 castor oil, polyoxyl 40 castor oil, polysorbate 20, polysorbate 60, polysorbate 80 and polyglycerol esters of fatty acids.

In an embodiment of the present invention, the antioxidant is selected from one or more of Lecithin, ascorbyl palmitate, d alpha-tocopherol, dl-alpha-tocopherol, d-alpha-Tocopheryl acetate, dl-alpha-Tocopheryl acetate, d-alpha-Tocopheryl acid succinate, dl alpha-Tocopheryl acid succinate, Vitamin E and derivatives thereof, Olive polyphenols and Algal polyphenols.

In an embodiment of the present invention, the composition further comprises an excipient. Preferably, the excipient is selected from one or more of Colloidal silica, Corn starch, Hydroxypropylmethylcellulose (HPMC), Maltodextrin, Magnesium stearate, Magnesium hydroxide, Microcrystalline cellulose, dextrin, sorbitol, mannitol and Trehalose.

In an embodiment of the present invention, the water-dispersible composition comprises at least one Omega-3 source, from 10% to about 90% by weight, and one or more of at least one carrier oil, up to about 70% by weight; at least one solvent, up to about 20% by weight; at least one emulsifier, up to about 30% by weight; and at least one antioxidant, up to about 0.01% by weight.

In an embodiment of the present invention, the water-dispersible composition comprises at least one Omega-3 source, from 80% to about 87% by weight, and one or more of at least one carrier oil, up to about 11% by weight; at least one solvent, up to about 10% by weight; at least one emulsifier, up to about 11% by weight; and at least one antioxidant, up to about 0.1% by weight.

In an embodiment of the present invention, the water-dispersible composition comprises at least one Omega-3 source, at about 87% by weight; at least one solvent, at about 9.75% by weight; and at least one emulsifier, at about 3.25% by weight.

In an embodiment of the present invention, the water-dispersible composition comprises at least one Omega-3 source, at about 85% by weight; at least one carrier oil, at about 2.25% by weight; at least one solvent, at about 2.25% by weight; at least one emulsifier, at about 10.48% by weight; and at least one antioxidant, at about 0.02% by weight.

In an embodiment of the present invention, the water-dispersible composition comprises at least one Omega-3 source, at about 80% by weight; at least one carrier oil, at about 10.5% by weight; at least one emulsifier, at about 9.4% by weight; and at least one antioxidant, at about 0.1% by weight.

In an embodiment of the present invention, the water-dispersible composition comprises at least one Omega-3 source, at about 85% by weight; at least one carrier oil, at about 4.8% by weight; at least one solvent, at about 4.8% by weight; at least one emulsifier, at about 4.9% by weight; and at least one antioxidant, at about 0.5% by weight.

In an embodiment of the present invention, the water-dispersible composition comprises at least one Omega-3 source, from 5% to about 70% by weight, and one or more of at least one carrier oil, up to about 45% by weight; at least one solvent, up to about 10% by weight; at least one emulsifier, up to about 15% by weight; and at least one antioxidant, up to about 0.01% by weight; wherein the composition further comprises an excipient from 30% to about 90% by weight.

BRIEF DESCRIPTION OF THE DRAWINGS

The invention will now be described with regards to the following drawings, which are as follows.

DETAILED DESCRIPTION OF THE PREFERRED EMBODIMENTS

Figure 1:
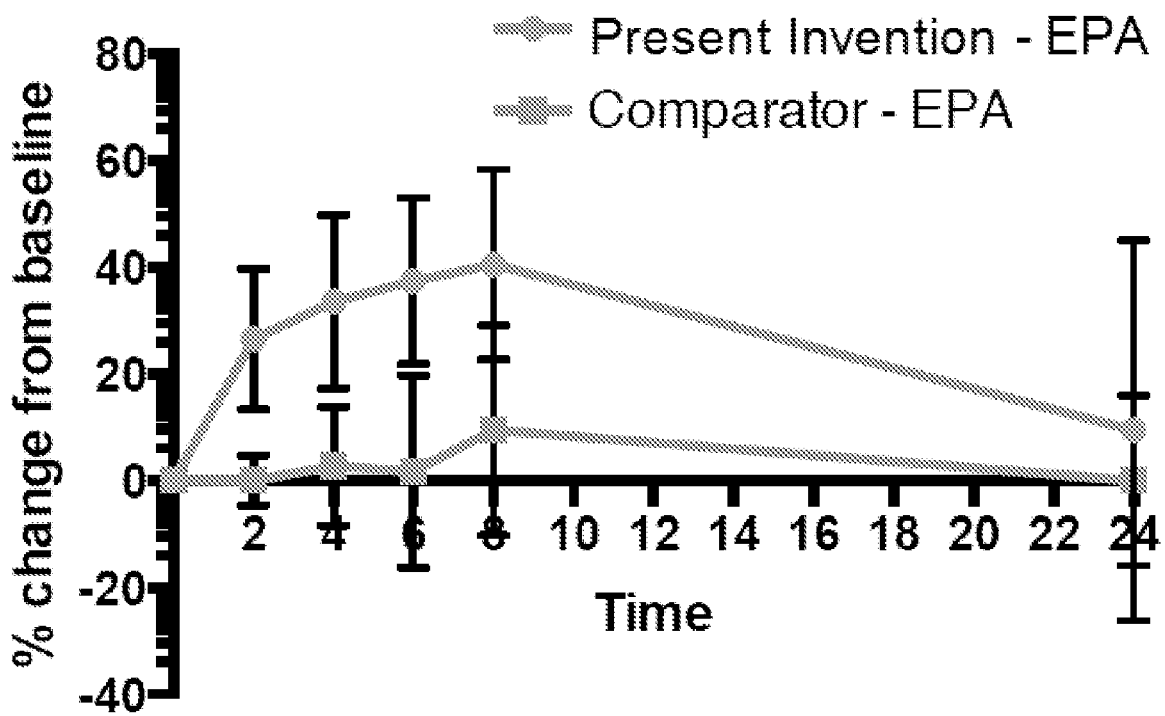
FIG. 1 is a graphical representation of the percentage uptake of an embodiment of the present invention containing EPA compared to a prior art means of delivering the same.

An aspect of the present invention provides for a water-dispersible composition comprising at least one source of Omega-3 and at least one micelle-promoting agent comprising one or more of a carrier oil, a solvent, an emulsifier and an antioxidant. In an embodiment of the present invention, the water-dispersible composition provides an advantageous delivery of Omega-3 upon ingestion, resulting in greater bioavailability of the Omega-3 to the body of the consumer. In an embodiment, this may allow for a greater percentage of the consumed Omega-3 to be absorbed by the body, which may allow for less total Omega-3 to need to be consumed in order to provide a beneficial effect.

In an embodiment of the present invention, the water-dispersible composition promotes at least a twofold increase in bioavailability of the Omega-3 source. This may mean that at least twice as much Omega-3 will be taken up by the body when delivered through the water-dispersible composition of an embodiment of the present invention, compared to prior art means of delivering an equal amount of Omega-3.

In a further embodiment, the composition of the present invention may promote at least a threefold increase in bioavailability of the Omega-3 source. In an even further embodiment, the composition of the present invention may promote at least a fourfold increase in bioavailability of the Omega-3 source, which may mean that at least four times as much Omega-3 will be taken up by the body when delivered through the water-dispersible composition of the present embodiment, compared to prior art means of delivering an equal amount of Omega-3.

In at least one embodiment of the present invention, the water-dispersible composition is adapted to form into micelles when in an aqueous environment. When the composition of the present invention is added to water—or a solution largely comprising water, such as milk or fruit juice—The Omega-3 fatty acids and the micelle-promoting agents may interact to form a population of micelles. These micelles may be stable with respect to temperature and acid effects in the stomach and reach the small intestine undamaged, attach themselves to the mucous membrane cells located across the inner surface of the small intestine, and may be absorbed, thereby leading to higher bio-availability than is the case for a "normal" fat digestion.

Case Study: Effect of Micelles on Bioavailability

Without wishing to limit the scope of the invention, it is believed that in order for aqueous-insoluble components (such as Omega-3) to be absorbed by the body, they need to be enveloped in a micelle that allows for the component to be dispersed in an aqueous environment. The micelle "package", with an outer layer that is adapted to interact with aqueous environments, may move through such an environment. In an aqueous environment such as that within the stomach and small intestine, the micelle "package" may be able to move to and attach to the mucous membrane cells located across the inner surface of the small intestine, where they may be easily absorbed by the body. However, the environment within the stomach is not conducive to the creation of micelles, as the micelle-promoting agents are typically present in insufficient amounts. As a result of this, a very large amount of an aqueous-insoluble component must typically be consumed in order for a sufficient quantity of it to be absorbed by the body.

The present invention seeks to overcome this by, in at least one embodiment, providing the necessary agents to promote the formation of micelles well before the Omega-3 passes the mucous membrane cells. In at least one embodiment, the composition of the present invention—upon dispersing within an aqueous environment—may arrange into micelles containing the Omega-3. This may allow for the micelles to be taken up by the body, allowing for the Omega-3 to be absorbed by the body with greater success. An example clinical trial comparing an embodiment of the present invention to a 'typical' delivery means of Omega-3 was conducted. 5 participants (3 males, 2 females) with an average age of 43 were included in the trial based on a power calculation to have an 80% chance of detecting a 50% increase in EPA compared to the control.

Inclusion criteria included otherwise healthy men and women between the ages of 18-60 years with a BMI lower than 30. Participants were excluded if they had previous history of hematological diseases (e.g., known susceptibility to thrombosis), pathological laboratory status (blood count, thrombocytes), were on medication for diabetes, heart disease, cholesterol or blood pressure, had known disorders of the heart, kidney, lung, skin or liver function, diagnosed with cancer, food allergies or intolerances, or had participated in another study in the last 6 months.

TABLE 1

Percentage Composition of Micelle-Prepared Capsules

| Common name/trade name | Wt. % |
|---|---|
| Omega-3 fish oil ethyl ester (72 wt. % EPA, 28 wt. % DHA) | 87% |
| Micelle Additive (Composition below) | 13% |
| Micelle Additive Composition | |
| Polysorbate 80 | 50% |
| Polyoxyl 40 (hyd. castor oil) | 25% |
| Polyethylene Glycol 400 | 12.5% |
| *Citrus* oil (>90% d-limonene) | 12.5% |

A randomised, cross-over, non-blinded study design was used with a 7-week washout period between consumption of each of the treatments. Group A consumed 2 micelle-prepared Omega-3 ethyl ester hard gelatin capsules, with the active ingredients in proportion as per Table 1, above. Each capsule contained 345 mg EPA and 135 mg DHA. A total of 690 mg EPA and 270 mg DHA was delivered as a single dose. Group B, the control product, consumed 2 standard Omega-3 ethyl ester hard gelatin capsule. Each capsule containing 345 mg EPA and 135 mg DHA. A total of 690 mg EPA and 270 mg DHA was delivered as a single dose. The groups were reversed after the 7 week wash out period. The treatment dose was consumed immediately after taking a fasted blood sample. Blood samples were taken at 0, 2, 4, 6, 8 and 24 h for each of the treatment groups. All meals were provided and scheduled and excluded foods with known high Omega-3 content. A list of foods and supplements to be avoided was also provided to all the participants for the evening meal.

Figure 2:
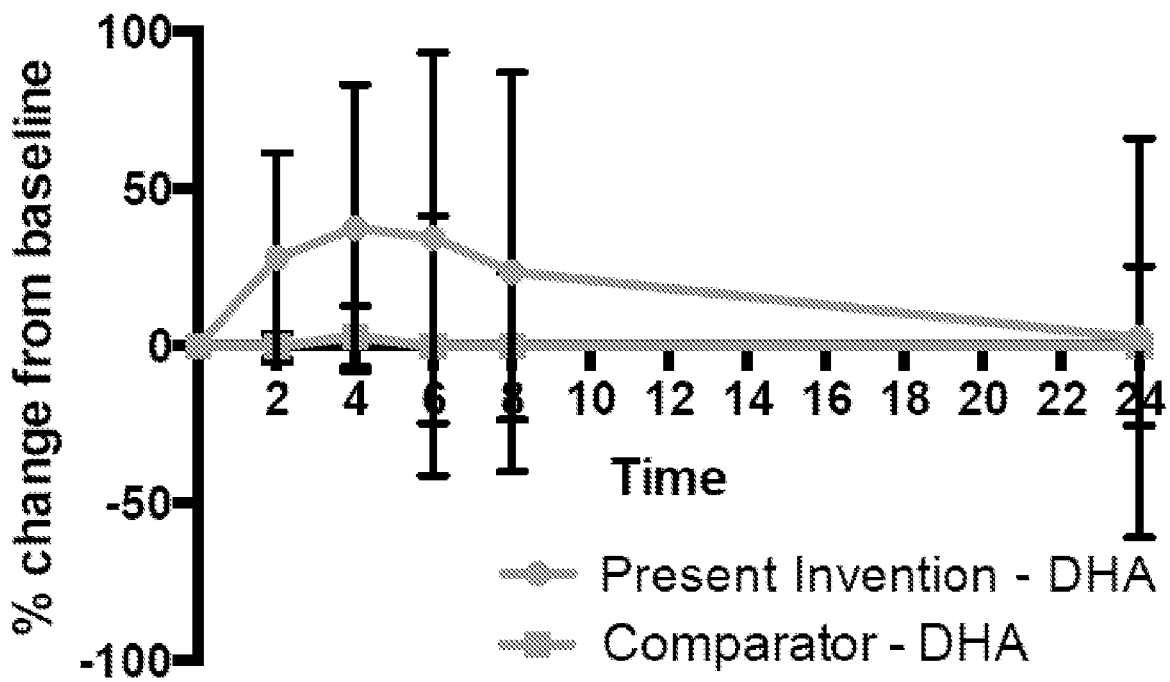
FIG. 2 is a graphical representation of the percentage uptake of an embodiment of the present invention containing DHA compared to a prior art means of delivering the same.

EPA and DHA were measured as part of the total fatty acid profile and results were calculated as change in relative % of EPA & DHA compared to baseline. Data is presented as means with their standard errors in FIGS. 1 and 2—the comparative results for EPA are shown in FIG. 1 and the comparative results for DHA are shown in FIG. 2. The $AUC_{0-24}$ value (Area under the curve from 0 to 24 hours) represents the total bio-availability of the particular compound over the relevant period of time and is calculated using the data shown in FIGS. 1 and 2.

As shown in FIG. 1, in both the Micelle and Control groups the percentage of EPA in the plasma rose steadily from 0 to 8 h with a decrease back to near baseline at 24 hours. $C_{max}$ occurred at 8 hours (Δ 0.406 Micelle-prepared, Δ 0.124 control). The average percentage change from baseline EPA concentration was significantly different in the Micelle group (p=0.0198) with a difference in $AUC_{0-24}$ of approximately 4.65 times compared to the control product.

As is shown in FIG. 2, the DHA results had a much higher variation in results than the EPA with an overall very low uptake in the control group. This may be due to the lower concentration of the initial dose. The average percentage change from baseline DHA concentration was significantly different in the Micelle group (p=0.0258) with a difference in $AUC_{0-24}$ of approximately 4.3 times compared to the control product. $T_{max}$ occurred at 4 hours for both groups.

As a result of the above study, it has been shown that at least an embodiment of the present invention may aid in the ability of the body to take up Omega-3 fatty acids, with a total bio-availability over a 24-hour period that is several times greater than that of an Omega-3 supplement absorbed through "normal" digestive processes.

Micelle Diameter

Broadly, the composition of an embodiment of the present invention is such that, dispersed in an aqueous environment, the majority of micelles so formed will have diameters that are in the low-micrometre range (diameters less than 50 micrometres). In an embodiment of the present invention, the percentage composition of the water-dispersible composition is such that, dispersed in an aqueous environment, the composition forms a population of micelles with a mean population diameter of about 1 to 20 micrometres. In an embodiment, the mean population diameter may be less than about 15 micrometres. In an embodiment, the mean population diameter may be greater than about 5 micrometres. In an embodiment, the mean population diameter may be greater than about 10 micrometres. In a further embodiment, the mean population diameter may be between about 12 to 13 micrometres.

In an embodiment of the present invention, the percentage composition of the water-dispersible composition is such that, when dispersed in an aqueous environment, at least 50% of the population of micelles may have a diameter less than about 40 micrometres. In an embodiment, at least 70% of the population of micelles may have a diameter less than about 40 micrometres. In an embodiment, at least 90% of the population of micelles may have a diameter less than about 40 micrometres. In an embodiment, at least 95% of the population of micelles may have a diameter less than about 40 micrometres.

In an embodiment of the present invention, the percentage composition of the water-dispersible composition is such that, when dispersed in an aqueous environment, at least 20% of the population of micelles may have a diameter less than about 10 micrometres. In an embodiment, at least 30% of the population of micelles may have a diameter less than about 10 micrometres. In an embodiment, at least 40% of the population of micelles may have a diameter less than about 10 micrometres.

In an embodiment of the present invention, the low-micrometre micelles are sufficiently small so as to interact with the mucous membrane cells lining the small intestine.

Figure 3:
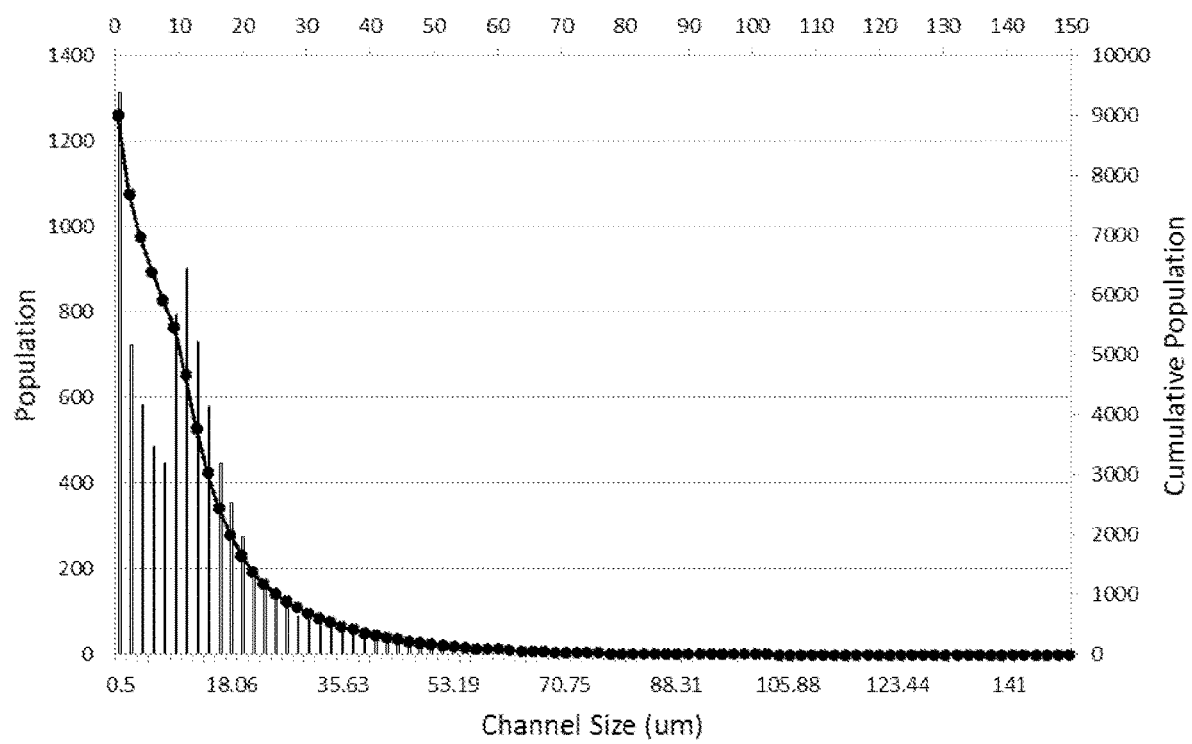
FIG. 3 is a graph of the population and cumulative population of micelles formed through the dispersion of an embodiment of the present invention to 200 mg/L in an aqueous solvent.

The micelle population size distribution for an embodiment of the present invention dispersed in water to a concentration of 200 mg/L is shown in FIG. 3. In the graph shown therein, the population of micelles that pass through a particular channel size is shown by the vertical lines and is graphed against the left vertical axis, while the cumulative population of micelles that are larger than the channel size are graphed by the curved line against the right vertical axis. In the particular embodiment shown, the population mean micelle diameter is approximately 12.41 micrometres. In the particular embodiment, approximately 90% of the population of micelles are smaller than 26.67 micrometres. In the particular embodiment, approximately 43% of the population of micelles are smaller than 10 micrometres, with 10% of the population of micelles smaller than 1.7 micrometres. The graph of FIG. 3, which extends out to a channel size of approximately 150 micrometres, represents the distribution of approximately 99.99% of the micelle population formed through the embodiment of the present invention.

Although the experimental data of FIG. 3 is obtained at a composition concentration of 200 mg/L in water, the concentration of a micelle-forming substance dispersed in water has minimal effect on the size of micelles formed by said substance. Therefore, the data shown in FIG. 3 is equally applicable to an embodiment of the present invention dispersed in an aqueous environment at any therapeutic dosage amount.

From FIG. 3, it can be concluded that at least an embodiment of the present invention produces a population of micelles with a mean population diameter between 12 and 13 micrometres.

Case Study: Micelle Diameter and Bio-Availability

The percentage composition of micelle-promoting agents is known to determine the resulting mean diameter and range of the micelle population. It has been further determined that the diameter of a particular micelle unit is likely to have a distinct and significant effect on the ability of the body to absorb the micelle. Without wishing to limit the scope of the invention, it is theorised that the smaller a micelle is, the more readily it is taken up by the body.

An example clinical trial utilising different compositions of the present invention for delivery of Omega-3 was conducted. 5 participants (3 males, 2 females) with an average age of 43 were included in the trial based on a power calculation to have an 80% chance of detecting a 50% increase in EPA compared to the control. Inclusion criteria included otherwise healthy men and women between the ages of 18-60 years with a BMI lower than 30. Participants were excluded if they had previous history of hematological diseases (e.g., known susceptibility to thrombosis), pathological laboratory status (blood count, thrombocytes), were on medication for diabetes, heart disease, cholesterol or blood pressure, had known disorders of the of heart, kidney, lung, skin or liver function, diagnosed with cancer, food allergies or intolerances, or had participated in another study in the last 6 months. The concentration of Omega-3 fatty acids in the blood plasma of each group was measured over a period of 24 hours, the results of which are tabulated below and shown graphically in FIG. 4.

TABLE 2

| | Blood Plasma Concentration over 24 hours | | | | | | | | | |
|---|---|---|---|---|---|---|---|---|---|---|
| | Time (hr) | | | | | | | | | |
| | 0 | 1 | 2 | 3 | 4 | 5 | 6 | 7 | 8 | 24 |
| Conc. Study 1 | 0 | 0.12 | 0.23 | 0.29 | 0.35 | 0.36 | 0.37 | 0.39 | 0.41 | 0.18 |
| Conc. Study 2 | 0 | 0.04 | 0.07 | 0.11 | 0.21 | 0.25 | 0.3 | 0.34 | — | 0.15 |

The mean size of the micelle population in Conc. Study 1 is 17.7 micrometres, while the mean size of the micelle population in Conc. Study 2 is 27.4 micrometres.

TABLE 3

Statistical Results of Clinical Concentration Studies

| | Conc. Study 1 | Conc. Study 2 |
|---|---|---|
| Baseline | 0.0 | 0.0 |
| Total Area ($AUC_{0-24}$) | 7.035 | 5.315 |
| Total Peak Area | 7.035 | 5.315 |
| Number of Peaks | 1.000 | 1.000 |
| First X | 0.0 | 0.0 |
| Last X | 24.00 | 24.00 |
| Peak X | 8.000 | 7.000 |
| Peak Y | 0.4100 | 0.3400 |
| Area | 7.035 | 5.315 |

Figure 4:
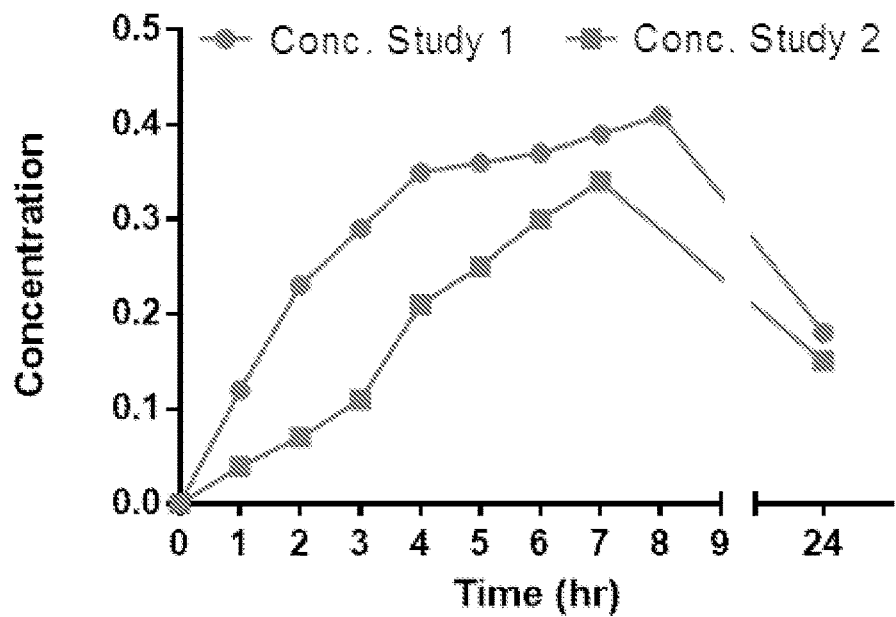
FIG. 4 is a graphical representation of the percentage uptake of an embodiment of the present invention with a smaller mean micelle diameter compared to an embodiment of the present invention with a larger mean micelle diameter.

As Table 3 above shows, and as shown in the graph of FIG. 4, the $AUC_{0-24}$ of the first clinical concentration study is 7.035, while the $AUC_{0-24}$ for the second clinical concentration study is 5.315. As micelle size increases, this difference becomes even more apparent; for a mean size of approximately 50 micrometres, the $AUC_{0-24}$ is approximately 2.0. Therefore, it is apparent that decreasing micelle size promotes an increased $AUC_{0-24}$, which is equivalent to an increase in bioavailability of the delivered Omega-3.

The clear advantage of the present invention is therefore not only in the provision of Omega-3 through micelles, but in the formation of micelles of reduced size in order to improve the ability of the micelles to deliver the Omega-3 to the body.

However, whilst the above example suggests that a decreasing mean micelle diameter can be inversely linked to an increasing uptake of Omega-3, there is a limit beyond which this uptake may become dangerous. Every substance, including therapeutic and dietary substances, has a toxicity concentration—a concentration in the body beyond which the substance is no longer beneficial and now poses danger to the person. Fat soluble substances, such as Omega-3, are ordinarily of no concern; their uptake is so minimal that an ordinary diet is extremely unlikely to induce Omega-3 toxicity in a person. The human body can utilise nanometre-scale micelles in the capture of these fat-soluble substances because, as has been discussed previously, the time delay involved in the natural construction of the micelles means that only a very small percentage of the consumed substance will be successfully absorbed by the body. Therefore, an extremely rapid capture and uptake process is beneficial.

However, embodiments of the present invention may allow for a far larger proportion of the consumed Omega-3 to be captured and taken up by the body. There is, therefore, the danger that uptake will be too rapid and may induce toxicity, particularly if the person is consuming multiple types of dietary supplements or therapeutic agents.

As is shown in FIGS. 1 & 2, the embodiments of the present invention have been determined as providing a balance between the uptake and absorption of Omega-3 by the body and avoidance of toxicity concerns. The shape of both FIGS. 1 & 2 indicates that the uptake of Omega-3 is both high and more importantly is consistently high and spread out over a 24-hour period. This may be compared to the potential over-delivery that may occur with sub-micrometre-scale micelle formation; although the $AUC_{0-24}$ of the resulting graph (for the uptake of Omega-3 delivered by sub-micrometre-scale micelles) may be much higher, it is highly likely that essentially all of the delivery would occur in a very short period of time, leading to a massive increase in concentration of Omega-3 in the body which may reach potentially toxic levels.

The embodiments of the present invention, providing for a population of micelles substantially in the range of 0.5-50 micrometres in diameter and with a mean diameter of 1-20 micrometres, have been thus identified as providing the safest, most consistent means of delivering a therapeutically-effective dosage of Omega-3 to the human body.

Composition of the Invention

In an embodiment of the present invention, the Omega-3 source may comprise at least one Omega-3 fatty acid selected from one or more of eicosapentaenoic acid (EPA), docosahexaenoic acid (DHA), docosapentaenoic acid (DPA) and alpha-linolenic acid (ALA). In an embodiment, the Omega-3 source is an Omega-3 fatty acid that is present in one or more forms selected from fatty acids, ethyl esters of fatty acids, triglycerides of fatty acids and phospholipids of fatty acids. The source of the Omega-3 fatty acids, such as EPA, DHA, DPA and ALA, may be selected from one or more of fish oil ethyl esters, fish oil triglycerides, natural fish oils, algae oils, krill oils, green-lipped mussel oil, calamari oil/squid oil and other naturally-occurring Omega-3 sources. Different Omega-3 fatty acid sources are approved for pharmaceutical and/or supplementary use in different jurisdictions. Therefore, the source may be changed, or may be present in another form or derivative that is not specifically listed above, without departing from the object of the invention.

The skilled person may recognise that Omega-3 sources, such as those identified above, may comprise any number of additional compounds. The skilled person will understand that the Omega-3 source within the composition of the present invention may comprise trace impurities, which may be characteristic impurities of the Omega-3 source.

The question of the presence or absence of trace impurities within the Omega-3 source will be understood by the skilled addressee as having no effect on the scope of the invention as claimed, provided that the water-dispersible composition created still fulfils the object of the invention—that being the creation of a composition providing at least twofold increase in bioavailability of Omega-3 through the promotion of micelle formation. In other words, the inclusion of an impurity within the Omega-3 source that does not inhibit the ability of the resulting composition to provide at least a twofold increase in bioavailability would be regarded by the skilled person as being within the scope of the object of the invention.

In an embodiment, the carrier oil may be selected from one or more of medium chain triglycerides, long-chain triglycerides, caprylic and/or capric triglycerides, coconut oil, corn oil, cottonseed oil, olive oil, sesame oil, soybean oil, peanut oil, castor oil, fish oil and oleic acid.

In an embodiment, the solvent may be selected from one or more of citrus oil, ethanol, ethyl oleate, glycerine, glyceryl mono-oleate, limonene, polyethylene glycol 300, polyethylene glycol 400, polyethylene glycol 600 and propylene glycol.

In an embodiment, the emulsifier may be selected from one or more of hydrogenated castor oil, lecithin, macrogolglycerol hydroxystearate, oat oil polar lipids, phosphatidylcholine, poloxamers, polyoxyl 35 castor oil, polyoxyl 40 castor oil, polysorbate 20, polysorbate 60, polysorbate 80 and polyglycerol esters of fatty acids.

In an embodiment, the antioxidant may be selected from one or more of Lecithin, ascorbyl palmitate, d-alpha-tocopherol, dl-alpha-tocopherol, d-alpha-Tocopheryl acetate, dl-alpha-Tocopheryl acetate, d-alpha-Tocopheryl acid succinate, dl-alpha-Tocopheryl acid succinate, Vitamin E and derivatives thereof, Olive polyphenols and Algal polyphenols.

Not all embodiments may comprise a micelle-promoting agent from all categories. Certain embodiments may comprise, in addition to the Omega-3 source and any other supplementary additives, only a carrier oil, only a solvent, only an emulsifier or only an antioxidant. Certain embodiments may comprise any two of the micelle-promoting agent categories. Certain embodiments may comprise any three of the micelle-promoting agent categories. Compositional ranges for the constituents of some embodiments of the present invention are shown in the table below:

TABLE 4

Percentage Composition Range for Liquid Delivery

| Component | % Composition |
|---|---|
| Omega-3 Fatty Acid | 10-90 wt. % |
| Carrier Oil | 0-70 wt. % |
| Solvent | 0-20 wt. % |
| Emulsifier | 0-30 wt. % |
| Antioxidant | 0-0.5 wt. % |

Several example compositions are shown in the table below. Each of these have been determined to fulfil at least an object of the invention:

TABLE 5

Example Compositions of an embodiment for Liquid Delivery

| Component | % Comp. 1 | % Comp. 2 | % Comp. 3 | % Comp. 4 |
|---|---|---|---|---|
| Omega-3 Source | 87% | 85% | 80.00% | 85.00% |
| Carrier Oil | — | 2.26% | 10.50% | 4.80% |
| Solvent | 9.75% | 2.25% | — | 4.80% |
| Emulsifier | 3.25% | 10.47% | 9.40% | 4.90% |
| Antioxidant | — | 0.02% | 0.10% | 0.50% |

As shown in the table above, not every micelle-promoting agent type is always needed. In particular, certain forms of micelle-promoting agent of one type may also serve to fulfil the purpose of another type. For example, certain carrier oils may also serve as Omega-3 solvents, and vice-versa; likewise, particular solvents may also serve as emulsifiers, and vice-versa; finally, certain carrier oils may also serve as emulsifiers, and vice-versa.

Certain embodiments of the present invention may comprise additional additives without departing from the object of the invention, provided that said object is still met—that being the creation of a composition providing at least twofold increase in bioavailability of Omega-3 through the promotion of micelle formation.

According to a further embodiment of the invention, a solid composition may be produced by allowing the active-ingredient-containing composition to be adsorbed in or carried on an excipient. Any type of excipient capable of adsorbing or carrying the liquid composition and acceptable for oral administration can be used for this purpose. In an embodiment, the excipient may be selected from one or more of colloidal silica, corn starch, hydroxypropylmethylcellulose (HPMC), maltodextrin, magnesium stearate, magnesium hydroxide, microcrystalline cellulose, dextrin, sorbitol, mannitol and trehalose.

Different excipients may offer advantages for different uses of the present invention. For example, if sorbitol, dextrin and/or mannitol are used as an excipient, the solid composition becomes soluble in water. If lactose, cornstarch, sorbitol, and/or crystalline cellulose are used, the solid composition acquires plasticity and can be directly compacted into tablet form. Moreover, chewable tablets, differentially soluble tablets, foaming tablets and the like can be prepared accordingly. In other embodiments of the invention, the composition can be used in the preparation of liquids, pastes and emulsions. For preparing the solid composition, any conventional auxiliaries such as a binder, a disintegrator, a dispersant, an antiseptic and a lubricant may be used. In an embodiment of the present invention, the binder may be one a water-soluble binder such as polyvinylpyrrolidone, hydroxypropyl cellulose, polyvinyl alcohol, hydroxypropyl methylcellulose, methylcellulose, Pullulan, syrup, sodium alginate, agar, gelatin, soybean polysaccharide, gum arabic and the like.

The preferable compositional range of the present invention is shown in the table below for an embodiment of the present invention intended for delivery in a solid form, such as powders for dissolution or other purposes, hard tablets or similar:

TABLE 6

Percentage Composition Range for Solid Delivery

| Component | % Composition |
|---|---|
| Omega-3 Fatty Acid | 5-70 wt. % |
| Carrier Oil | 0-45 wt. % |
| Solvent | 0-10 wt. % |
| Emulsifier | 0-15 wt. % |
| Antioxidant | 0-0.01 wt. % |
| Excipient | 30-90 wt. % |

Method of Production

For the preparation of the composition of this invention, the Omega-3 source is combined with one or more of carrier oils, solvents, emulsifiers and antioxidants. The Omega-3 active ingredients derived from the relevant Omega-3 source may be used in either their 'natural' state as fatty acids, as ethyl esters, as triglycerides or as phospholipids or in the form of one or more other derivatives of Omega-3 fatty acids.

The components are combined with the micelle-promoting agents in order to produce a composition that, when dispersed into an aqueous environment, the formation of micelles with a mean diameter of about 1-20 micrometres is promoted. An embodiment of the present invention may be further combined with one or more excipients in order to produce a solid form of the present invention.

An embodiment of the present invention may be directly consumed by a person or animal as a hard or soft tablet, gel capsule or similar direct consumption means. Alternatively, the embodiment may be combined with an aqueous liquid, such as water, juice or milk, wherein it may be dispersed throughout and then consumed by the person or animal.

While the invention has been described with reference to preferred embodiments above, it will be appreciated by those skilled in the art that it is not limited to those embodiments, but may be embodied in many other forms, variations and modifications other than those specifically described. The invention includes all such variation and modifications. The invention also includes all of the steps, features, components and/or devices referred to or indicated in the specification, individually or collectively and any and all combinations or any two or more of the steps or features.

Although the invention has been described with reference to particular chemicals, these identified chemicals should be only regarded as examples within their particular chemical family as opposed to a complete and exhaustive list of possible ingredients. The skilled person will appreciate that unless otherwise specified, the mere substitution of one particular chemical for another with similar uses, effect, chemical formulae, pharmaceutical capability, biological compatibility or otherwise similar properties falls within the scope or object of the invention described herein, and that the scope of the invention includes any and all of these substitute chemicals insofar as the object of the invention is still fulfilled.

In this specification, unless the context clearly indicates otherwise, the word "comprising" is not intended to have the exclusive meaning of the word such as "consisting only of", but rather has the non-exclusive meaning, in the sense of "including at least". The same applies, with corresponding grammatical changes, to other forms of the word such as "comprise", etc.

Other definitions for selected terms used herein may be found within the detailed description of the invention and apply throughout. Unless otherwise defined, all other scientific and technical terms used herein have the same meaning as commonly understood to one of ordinary skill in the art to which the invention belongs.

INDUSTRIAL APPLICABILITY

The present invention may be utilised in relation to compounds and compositions for use as therapeutics, complementary medicines and cosmetics. In particular, the water-dispersible compounds of the present invention, comprising one or more of eicosapentaenoic acid (EPA), docosahexaenoic acid (DHA), docosapentaenoic acid (DPA) and alpha-linolenic acid (ALA) and having high bioavailability, are effective in clinical, therapeutic, functional food and cosmetic application.

The invention claimed is:

1. A water-dispersible composition comprising:
   at least one source of Omega-3 fatty acid comprising eicosapentaenoic acid (EPA); and
   micelle-promoting agents comprising a carrier oil, a solvent, and an emulsifier;
   wherein the composition comprises up to 70% of the carrier oil by weight and the carrier oil comprises medium chain triglycerides,
   wherein the composition comprises up to 20% of the solvent by weight and the solvent comprises citrus oil,
   wherein the composition comprises up to 30% of the emulsifier by weight and the emulsifier comprises lecithin, and
   wherein the composition promotes at least a twofold increase in bioavailability of the Omega-3 fatty acid source.

2. The water-dispersible composition of claim 1 wherein the composition promotes at least a threefold increase in bioavailability of the Omega-3 fatty acid source.

3. The water-dispersible composition of claim 1 wherein the composition promotes at least a fourfold increase in bioavailability of the Omega-3 fatty acid source.

4. The water-dispersible composition of claim 1 wherein the percentage composition of the Omega-3 fatty acid source and the at least one micelle-promoting agent in the water-dispersible composition is such that, when dispersed in an aqueous environment, the Omega-3 fatty acid source and at least one micelle-promoting agent form a population of micelles with a mean population diameter of about 1 to 20 micrometers.

5. The water-dispersible composition of claim 4 wherein the mean population diameter of the micelles is less than 15 micrometers and greater than about 5 micrometers when dispersed in an aqueous environment.

6. The water-dispersible composition of claim 5, wherein the mean population diameter of the micelles is between about 12 to 13 micrometers when dispersed in an aqueous environment.

7. The water-dispersible composition of claim 4 wherein the percentage population of micelles with a diameter of less than 10 micrometers is greater than 20%.

8. The water-dispersible composition of claim 4, wherein the percentage population of micelles with a diameter of less than 10 micrometers is greater than 40%.

9. The water-dispersible composition according to claim 1, wherein the Omega-3 fatty acid source comprises at least two Omega-3 fatty acids selected from eicosapentaenoic acid (EPA), docosahexaenoic acid (DHA), docosapentaenoic acid (DPA) and alpha-linolenic acid (ALA).

10. The water-dispersible composition according to claim 9, wherein the Omega-3 fatty acid is present in one or more forms selected from fatty acids, ethyl esters, triglycerides and phospholipids.

11. The water-dispersible composition according to claim 1, wherein the water-dispersible composition further comprises an antioxidant, wherein the antioxidant is selected from one or more of lecithin, ascorbyl palmitate, d-alpha-tocopherol, dl-alpha-tocopherol, d-alpha-Tocopheryl acetate, dl-alpha-Tocopheryl acetate, d-alpha-Tocopheryl acid succinate, dl-alpha-Tocopheryl acid succinate, Vitamin E and derivatives thereof, Olive polyphenols, Algal polyphenols, and mixtures thereof.

12. The water-dispersible composition according to claim 1, further comprising an excipient.

13. The water-dispersible composition of claim 12, wherein the excipient is selected from one or more of Colloidal silica, Com starch, Hydroxypropylmethylcellulose (HPMC), Maltodextrin, Magnesium stearate, Magnesium hydroxide, Microcrystalline cellulose, dextrin, sorbitol, mannitol and Trehalose.

14. A water-dispersible composition according to claim 1, comprising at least one Omega-3 fatty acid source, from 80% to about 87% by weight, and:
   at least one carrier oil, up to about 11% by weight;
   at least one solvent, up to about 10% by weight;
   at least one emulsifier, up to about 11% by weight; and at least one antioxidant, up to about 0.1% by weight.

15. The water-dispersible composition of claim 14, comprising:
   the at least one Omega-3 fatty acid source, at about 87% by weight;
   the at least one solvent, at about 9.75% by weight; and the at least one emulsifier, at about 3.25% by weight.

16. The water-dispersible composition of claim 14, comprising:
   the at least one Omega-3 fatty acid source, at about 85% by weight; the at least one carrier oil, at about 2.25% by weight;
   the at least one solvent, at about 2.25% by weight;
   the at least one emulsifier, at about 10.48% by weight; and the at least one antioxidant, at about 0.02% by weight.

17. The water-dispersible composition of claim 14, comprising:
   the at least one Omega-3 fatty acid source, at about 80% by weight; the at least one carrier oil, at about 10.5% by weight;
   the at least one emulsifier, at about 9.4% by weight; and the at least one antioxidant, at about 0.1% by weight.

18. The water-dispersible composition of claim 14, comprising:
   the at least one Omega-3 fatty acid source, at about 85% by weight; the at least one carrier oil, at about 4.8% by weight;
   the at least one solvent, at about 4.8% by weight;
   the at least one emulsifier, at about 4.9% by weight; and the at least one antioxidant, at about 0.5% by weight.

19. The water-dispersible composition of claim 1, comprising at least one Omega-3 fatty acid source, from 5% to about 70% by weight, and:
   at least one carrier oil, up to about 45% by weight;
   at least one solvent, up to about 10% by weight;
   at least one emulsifier, up to about 15% by weight; and
   at least one antioxidant, up to about 0.01% by weight;
   wherein the composition further comprises an excipient from 30% to about 90% by weight.

\* \* \* \* \*